United States Patent [19]

Kaneko et al.

[11] Patent Number: 4,754,029

[45] Date of Patent: Jun. 28, 1988

[54] 3-OXO-2-AZABICYCLOHEXANE DERIVATIVES

[75] Inventors: Chikara Kaneko; Masayuki Sato; Nobuya Katagiri, all of Miyagi, Japan

[73] Assignee: Eisai Co., Ltd., Tokyo, Japan

[21] Appl. No.: 844,011

[22] Filed: Mar. 26, 1986

[30] Foreign Application Priority Data

Apr. 2, 1985 [JP] Japan ................... 60-68528

[51] Int. Cl.$^4$ ................ C07D 205/12; C07D 205/08; C07D 213/89; C07D 213/69
[52] U.S. Cl. ....................... 540/203; 204/157.71; 546/290; 546/296
[58] Field of Search ........................ 540/203

[56] References Cited

PUBLICATIONS

Kaneko et al, Tet. Letters 25, 1591 (1984).
Katagiri et al, Tet. Letters 25, 5665 (1984).

*Primary Examiner*—Mark L. Berch
*Attorney, Agent, or Firm*—Wenderoth, Lind & Ponack

[57] ABSTRACT

3-Oxo-2-azabicyclohexane derivatives represented by the general formula:

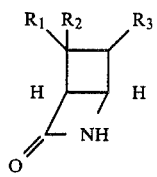

wherein $R_1$ represents an optically active menthoxy group or an optically active 1-phenylethoxy group when $R_2$ and $R_3$ are combined to form a bond; when $R_3$ is a hydrogen atom, $R_1$ and $R_2$ are combined to form an oxo group or, $R_2$ is a hydrogen atom and $R_1$ is a hydroxy group or a lower alkanoyloxy group. The 3-oxo-2-azabicyclohexane derivatives are novel compounds useful as intermediates for antibacterial agents.

5 Claims, No Drawings

3-OXO-2-AZABICYCLOHEXANE DERIVATIVES

BACKGROUND OF THE INVENTION

1. Field of the Invention

The present invention relates to novel compounds useful as intermediates for antibacterial agents.

2. Brief Description of the Prior Art

4-Substituted-azetidin-2-ones hitherto known as important intermediates for carbapenem antibacterial agents, as are shown in, e.g., *J. Am. Chem. Soc.*, vol. 103, page 2406 (1981), *Tetrahedron Lett.*, page 3009 (1983), *J. Org. Chem.*, vol. 45, page 1135 (1980), *J. Org. Chem.*, vol. 45, page 1143 (1980), etc. In the carbapenem skeleton, the following two isomers are present:

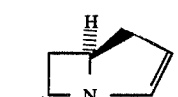

($\beta$-configuration)

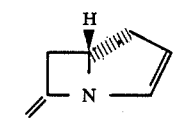

($\alpha$-configuration)

Of these, carbapenem derivatives having the $\beta$-configuration exhibit much higher antibacterial activity and carbapenem antibacterial agents including thienamycin which are presently under development all have this configuration. Therefore, compounds having a configuration capable of leading to carbapenems of this $\beta$-configuration are desired as intermediates; from a viewpoint of synthesis, however, it was difficult to obtain only 4-substituted-azetidin-2-one derivatives having a specific configuration in a simple manner and high yield. The present inventors have found that when the compounds of the present invention are used, 4-substituted-azetidin-2-one derivatives having a specific configuration can easily be obtained, and have accomplished the present invention.

SUMMARY OF THE INVENTION

Accordingly, an object of the present invention is to provide novel 3-oxo-2-azabicyclohexane derivatives having optical activity useful as intermediates for antibacterial agents and a process for production thereof.

PREFERRED EMBODIMENTS OF THE INVENTION

The compounds of the present invention are 3-oxo-2-azabicyclohexane derivatives represented by the general formula:

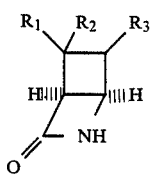

(I)

wherein $R_1$ represents an optically active menthoxy group or an optically active 1-phenylethoxy group when $R_2$ and $R_3$ form a bond; when $R_3$ is a hydrogen atom, $R_1$ and $R_2$ are combined to form an oxo group, or $R_2$ is a hydrogen atom and $R_1$ represents a hydroxy group or a lower alkanoyloxy group.

Examples of the optically active menthoxy group of $R_1$ in the general formula described above include l-menthoxy group [(1R,2S,5R)-menthoxy group], d-menthoxy group [(1S,2R,5S)-menthoxy group], (1S,2S,5R)-menthoxy group, (1R,2R,5S)-menthoxy group, etc. Further the optically active 1-phenylethoxy group represents (R)-1-phenylethoxy group or (S)-1-phenylethoxy group.

Examples of the lower alkanoyloxy group for $R_1$ include an acetoxy group, a propionyloxy group, an n-butyryl oxy group, an i-butyryloxy group, a valeryloxy group, an i-valeryloxy group, a pivaloyloxy group, etc.

The compounds of the present invention can be prepared by the following method.

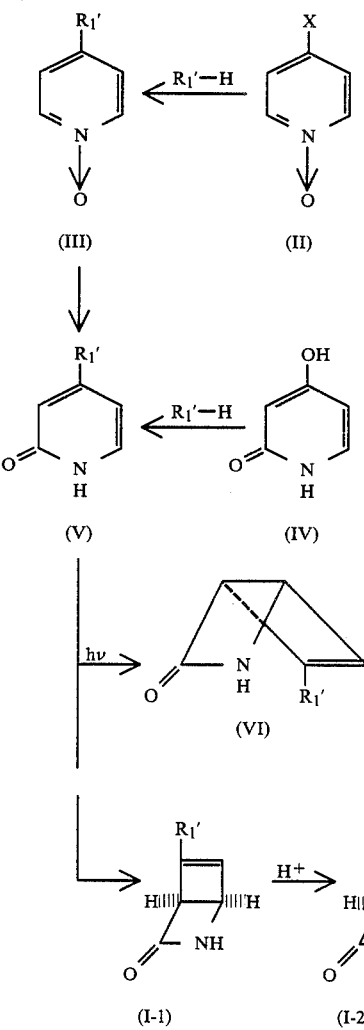

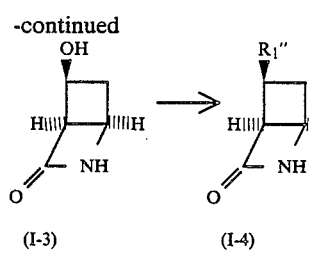

wherein X represents a nitro group or a halogen atom, R′₁ represents an optically active menthoxy group or an optically active 1-phenylethoxy group, and R″₁ represents a lower alkanoyloxy group.

As the optically active menthoxy group and optically active 1-phenylethoxy group shown by R′₁ and as the lower alkanoyloxy group shown by R″₁, groups similar to those shown for R₁ described above can be listed. Examples of the halogen atom shown by X include a chlorine atom, a bromine atom, etc.

The compound of general formula (III) can be obtained by reacting R′₁-H with the compound of general formula (II). For example, l-menthol, d-menthol, (R)-1-phenylethanol, (S)-1-phenylethanol, etc. are reacted with strong bases such as sodium hydride, potassium hydride, etc. to form alcoholates and then the alcoholates are reacted with the compound of general formula (II) to yield the compound of general formula (III). In this reaction, non-protonic polar solvents, for example, hexamethyltriamide phosphate, etc. can be used as solvents.

The compound of general formula (V) can be obtained by reacting acid anhydrides such as acetic anhydride, etc. with the compound of general formula (II) and then hydrolyzing the reaction product. Further, the compound of general formula (V) can also be obtained by reacting the compound of formula (IV) with R′₁-H. For example, the compound of formula (IV) is reacted with l-menthol, d-menthol, (R)-1-phenylethanol, (S)-1-phenylethanol, etc. in the presence of triaryl phosphines such as triphenyl phosphine, etc., or trialkyl phosphines such as tri(n-butyl) phosphine, etc. and azodicarboxylic acid esters such as diethyl azodicarboxylate, etc. to yield the compound of general formula (V).

By exposing the compound of general formula (V) to light, the compound of general formula (I-1) and the compound of general formula (VI) can be obtained. It is appropriate to use a light having a wavelength of 280 nm to 330 nm. As solvents, those having no absorption in this wavelength region are preferred. Preferred examples of the solvents include methanol, ethanol, ethyl ether, acetonitrile, toluene, benzene and a mixture thereof. Both isomers shown by general formula (I-1) and general formula (VI) can easily be separated from each other by utilizing the difference in solubility in solvents such as n-pentane. Further, the isomers can also be separated by means of liquid chromatography or silica gel chromatography.

The compound of formula (I-1) can be obtained by hydrolyzing the compound of general formula (I-1) with an acid. As the acid, mention may be made of hydrochloric acid, p-toluenesulfonic acid, trifluoroacetic acid, acidic ion exchange resin, etc. As the solvent, mention may be made of dioxane, ethyl ether, tetrahydrofuran, a mixture thereof or a mixture of these solvents with water.

The compound of formula (I-3) can be obtained by reducing the compound of formula (I-2). As a reducing agent, sodium borocyanohydride, etc. can be used.

The compound of general formula (I-4) can be obtained by acylating the compound of formula (I-3) with carboxylic acids shown by R″₁-H or reactive derivatives thereof, for example, acid anhydrides, acid chlorides, etc.

Using the compounds of the present invention, 4-substituted-azetidin-2-one derivatives can be prepared by the following method.

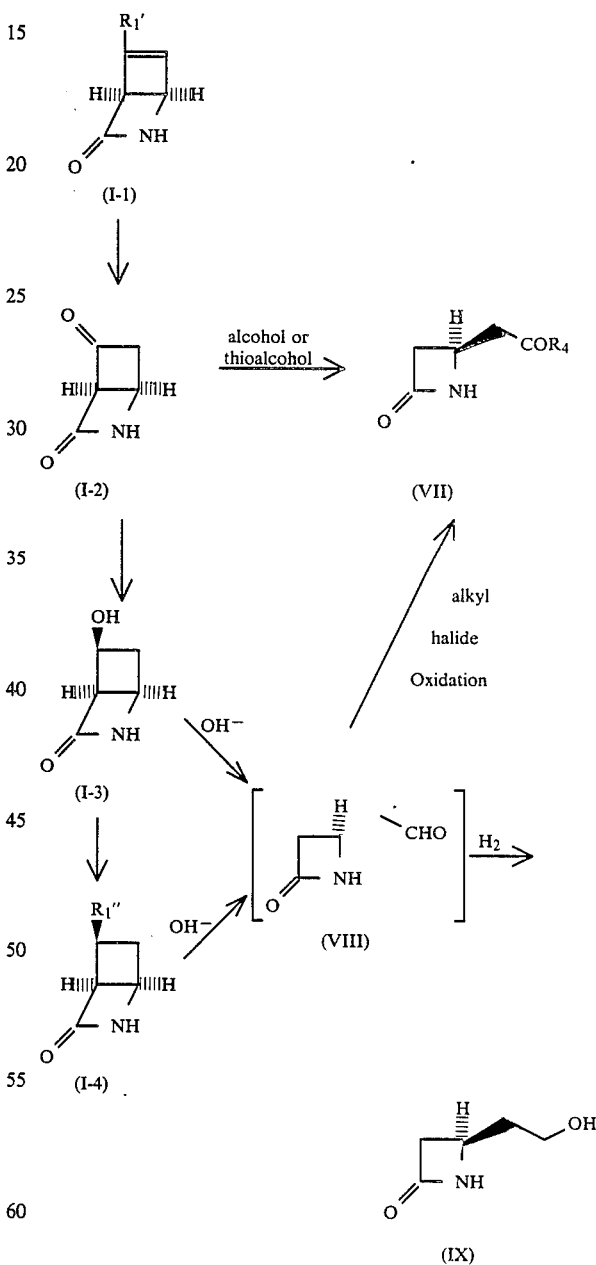

wherein R′₁ and R″₁ have the same significances as defined above and R₄ represents an ester residue.

A series of reactions from the compound of general formula (I-1) to the compound of general formula (I-4) are as described hereinbefore.

The 4-substituted-azetidin-2-one derivatives shown by general formula (VII) can be obtained by reacting the compound of general formula (I-2) with alcohols or thioalcohols, if necessary, in the presence of bases. Further, the compound of general formula (VII) can also be obtained, via the compound of general formula (VIII) (reaction intermediate, unstable), by treating the compound of general formula (I-3) or the compound of general formula (I-4) with a base such as potassium carbonate, etc. and an oxidizing agent such as potassium permanganate, etc. and then reacting the reaction product with an alkyl halide.

The 4-substituted-azetidin-2-one derivatives of general formula (IX) can be obtained, via the compound of general formula (VIII), by treating the compound of general formula (I-3) or the compound of general formula (I-4) with a base such as potassium carbonate, etc. and a reducing agent such as sodium boron hydride, etc.

The compound of general formula (VII) and the compound of general formula (IX) are known compounds as intermediates for carbapenem compounds, and various carbapenem compounds can be obtained from these compounds by known methods, for example, methods described in the publications supra.

Next, the present invention will be described in more detail with reference to the experiments and the examples below.

EXPERIMENT 1

4-[(l)-Menthoxy]pyridine N-oxide

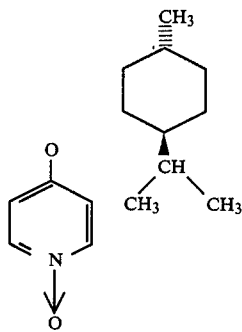

A mixture of 2.52 g of 60% oily sodium hydride, 9.36 g of (l)-menthol and 60 ml of phosphoric hexamethyltriamide was stirred on an oil bath of about 80° C. until evolution of hydrogen gas was discontinued. The solution was ice cooled and 8.4 g of 4-nitropyridine N-oxide was added thereto. The mixture was stirred for 30 minutes under ice cooling and then at room temperature overnight. The solvent was removed by distillation under reduced pressure and the residue was dissolved in benzene. The soluble matter was subjected to silica gel column chromatography [developing solvent: methanol-ethyl acetate (3:20, v/v)]. The resulting pale brown oily product was passed through and purified by an alumina column (40 g, developing solvent: chloroform) to obtain 11.69 g of the product.

Melting point: 60°~65° C.
Infrared absorption spectrum (cm$^{-1}$, chloroform): 1295
$^1$H-NMR (δ, CDCl$_3$): 0.60~2.33 (18H, m), 3.86~4.30 (1H, m), 6.81 (2H, d, J=8 Hz), 8.14 (2H, d, J=8 Hz),
Mass spectrum (M+): 249
Rotation [α]$_D^{27}$: −118.6° (c=1.3, chloroform)

EXPERIMENT 2

4-[(l)-Menthoxy]-2-pyridone

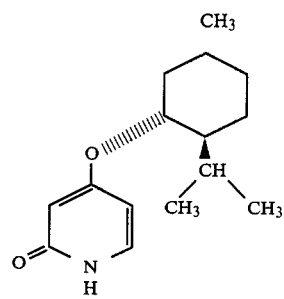

In 100 ml of acetic anhydride, 5.18 g of the compound obtained in Experiment 1 was heated for 1 hour and a half under reflux. The reaction mixture was concentrated under reduced pressure. A saturated aqueous solution of hydrogen sodium carbonate was added to the remaining oily substance and the mixture was stirred in a water bath for 30 minutes to render the system weakly alkaline. The separated oily substance was extracted with chloroform and anhydrous magnesium sulfate was added to the extract to dry it. The solvent was then removed by distillation and the residue was washed with diethyl ether to obtain crude crystals. The crude crystals were recrystallized from acetone-n-hexane to obtain 3.27 g of the desired product as needles.

Melting point: 220°~222° C.
Infrared absorption spectrum (cm$^{-1}$, chloroform): 3400~2500, 1640
$^1$H-NMR (δ, CDCl$_3$): 0.7~0.95 (9H, m), 1.00~2.32 (9H, m), 4.02 (1H, dt, J=3 Hz, 9 Hz), 5.88 (1H, s), 5.92 (1H, d, J=7 Hz), 7.19 (1H, d, J=7 Hz), 12.94 (1H, br)
Mass spectrum (M+): 249
Rotation [α]$_D^{28}$: −161.61° (c=1.24, chloroform)

EXPERIMENT 3

(S)-4-(1-Phenylethoxy)pyridine N-oxide

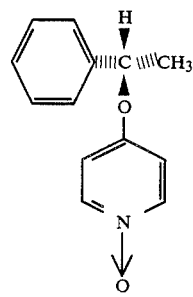

To a mixture of 210 mg of 60% oily sodium hydride and 8 ml of phosphoric hexamethyltriamide was added 610 mg of (S)-1-phenylethanol. The mixture was stirred at room temperature for 2 hours. After the mixture was cooled with ice water, 700 mg of 4-nitropyridine N-oxide was added thereto with stirring. The mixture was stirred for 30 minutes under ice cooling and then at room temperature overnight. The solvent was removed by distillation under reduced pressure and the residue was dissolved in benzene. The solution was purified by silica gel column chromatography [30 g, developing solvent: methanol-ethyl acetate (3:20, v/v)]. After the resulting crystals were decolored in ethyl acetate with activated charcoal, the crystals were recrystallized from ethyl acetate to obtain 775 mg of the product as needles.

Melting point: 134°~136° C.

1H-NMR (δ, CDCl3): 1.65 (3H, d, J=6 Hz), 5.30 (1H, q, J=6 Hz), 6.73 (2H, d, J=7 Hz), 7.33 (5H, s), 8.02 (2H, d, J=7 Hz)

Mass spectrum (M+): 215

Rotation [α]$_D^{29}$: −62.1° (c=1.09, chloroform)

EXPERIMENT 4

(R)-4-(1-Phenylethoxy)pyridine N-oxide

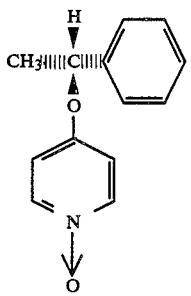

In a manner similar to Experiment 3, the product was obtained as needles in a yield of 73%, from 4-nitropyridine N-oxide and (R)-1-phenylethanol.

Melting point: 134°~136° C.

Rotation [α]$_D^{29}$: +62.1° (c=1.04, chloroform)

1H-NMR (CDCl3) spectrum was identical with that of Experiment 3

EXPERIMENT 5

(S)-4-(1-Phenylethoxy)-2-pyridone

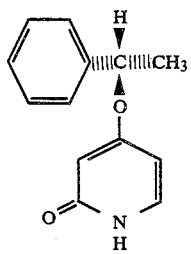

A mixture of 280 mg of the compound obtained in Experiment 3 and 5 ml of acetic anhydride was heated for 1 hour under reflux. The reaction mixture was concentrated under reduced pressure. A saturated aqueous solution of hydrogen sodium carbonate was added to the residue. The mixture was stirred in an ice bath for 30 minutes. The reaction solution was extracted with chloroform and anhydrous magnesium sulfate was added to the extract to dry it. The solvent was then removed by distillation and the crystals obtained were recrystallized from ethyl acetate to obtain 160 mg of the product.

Melting point: 151°~152° C.

Infrared absorption spectrum (cm⁻¹, KBr): 3300~2400, 1640

1H-NMR (δ, CDCl3): 1.63 (3H, d, J=6 Hz), 5.30 (1H, q, J=6 Hz), 5.76 (1H, d, J=2 Hz), 6.00 (1H, dd, J=2 Hz, 8 Hz), 7.16 (1H, d, J=8 Hz), 7.33 (5H, s), 13.0 (1H, br)

Mass spectrum (M+): 215

Rotation [α]$_D^{28}$: −169.7° (c=1.01, chloroform)

EXPERIMENT 6

(R)-4-(1-Phenylethoxy)-2-pyridone

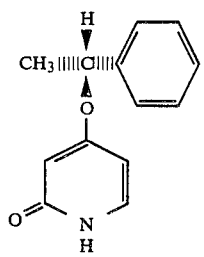

In a manner similar to Experiment 5, the product was obtained in a yield of 61%, from the compound obtained in Experiment 4.

Melting point: 151°~152° C.

Rotation [α]$_D^{28}$: +167.76° (c=1.03, chloroform)

Infrared absorption spectrum, 1H-NMR (CDCl3) spectrum and mass spectrum were identical with those of Experiment 5.

Experiment 7

4-[(1S,2S,5R)-Menthoxy]-2-pyridone

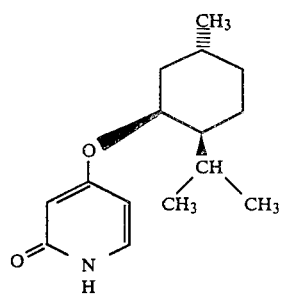

In 3 ml of hexamethylphosphoramide was dissolved 630 mg of triphenylphosphine. To the solution was dropwise added 418 mg of diethyl azodicarboxylate under ice cooling. After the temperature was elevated to room temperature and the mixture was stirred for 10 minutes, a hexamethylphosphoramide solution of 222 mg of 4-hydroxy-2-pyridone and 312 mg of (l)-menthol was dropwise added thereto under ice cooling. The reaction mixture was dissolved in 30 ml of ethyl ether. After washing with water, anhydrous sodium sulfate was added thereto to dry it. The solvent was removed by distillation under reduced pressure and the resulting residue was purified by silica gel column chromatography [developing solvent: ethyl acetate-methanol (3:1)] to obtain 240 mg of the product as colorless needles.

Melting point: 212°~214° C.

Infrared absorption spectrum (cm⁻¹, chloroform): 1650

1H-NMR (δ, CDCl3): 0.67~2.40 (18H, m), 4.67 (1H, m), 5.86~6.10 (2H, m), 7.23 (1H, d, J=10 Hz)

Rotation [α]$_D^{27}$: +109.71° (c=0.7, chloroform)

EXAMPLE 1

(1S,4R)-5-[(l)-Menthoxy]-3-oxo-2-azabicyclo[2.2.0]hexa-5-ene

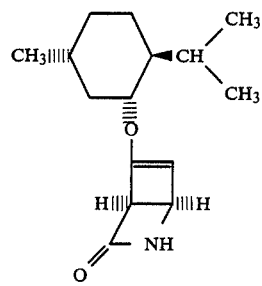

A solution of 1.0 g of the compound obtained in Experiment 2 in 500 ml of acetonitrile was irradiated with light (longer than 300 nm) for 4 hours and a half in an argon flow under ice cooling while stirring, using a high pressure mercury lamp of 400 W. The solvent was removed by distillation under reduced pressure and the residue was purified by silica gel column chromatography [5 g, developing solvent: ethyl ether] to obtain 0.99 g of crystals. The crystals were heated in 30 ml of n-pentane for a short period of time and insoluble matters were taken by filtration. The insoluble matters were recrystallized from n-hexane-ethyl ether to obtain 455 mg of the product as needles.

Melting point: 136°~137° C.

Infrared absorption spectrum (cm$^{-1}$, chloroform): 3410, 1755, 1615

$^1$H-NMR ($\delta$, CDCl$_3$): 0.72~2.20 (18H, m), 3.71 (1H, dt, J=4 Hz, 9 Hz), 4.23 (2H, m), 4.93 (1H, d, J=1 Hz), 6.15 (1H, br)

Mass spectrum (M+): 249

Rotation angle [$\alpha$]$^{27}$: +74.39° (c=1.38, chloroform)

Further, the crystals obtained by concentrating the n-pentane soluble matter obtained in the preparation step described above were recrystallized from n-hexane to obtain 369 mg of the following compound as needles:

(1R,4S)-5-[(l)-Menthoxy]-3-oxo-2-azabicyclo[2.2.0]hexa-5-ene

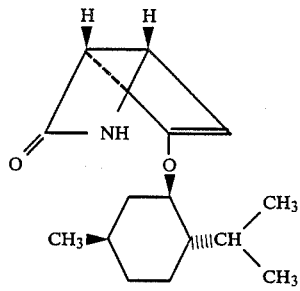

Melting point: 90°~91° C.

Infrared absorption spectrum (cm$^{-1}$, chloroform): 3410, 1755, 1615

$^1$H-NMR ($\delta$, CDCl$_3$): 0.73~2.20 (18H, m), 3.73 (1H, dt, J=4 Hz, 9 Hz), 4.21 (2H, m), 4.97 (1H, d, J=1 Hz), 6.19 (1H, br)

Mass spectrum (M+): 249

Rotation [$\alpha$]$_D^{28}$: −210.76° (c=1.23, chloroform)

EXAMPLE 2

(1R,4R)-3,5-Dioxo-2-azabicyclo[2.2.0]hexane

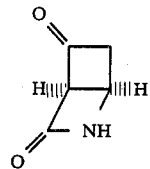

To a 2 ml tetrahydrofuran solution containing 19 mg of p-toluenesulfonic acid monohydrate and 50 mg of water was added 124.5 mg of (1S,4R)-5-[(l)-Menthoxy]-3-oxo-2-azabicyclo[2.2.0]hexa-5-ene obtained in Example 1. The mixture was stirred for 20 minutes at room temperature. In a small quantity of water was dissolved 8.4 mg of hydrogen sodium carbonate and the solution was added to the reaction mixture. After diluting with chloroform, anhydrous magnesium sulfate was added to dry it. The system was filtered and the filtrate was concentrated to dryness under reduced pressure to obtain crystals. After washing with a small quantity of n-pentane, the crystals were dried in vacuum in desiccator. Then the crystals were recrystallized from ethyl acetate-n-hexane to obtain 36 mg of the product as needles.

Melting point: 93°~95° C.

Infrared absorption spectrum (cm$^{-1}$, chloroform): 3420, 1800, 1760

$^1$H-NMR ($\delta$, CDCl$_3$): 3.20 (2H, d, J=3 Hz), 4.68 (1H, t, J=3 Hz), 4.48 (1H, q, J=3 Hz), 6.70 (1H, bs)

Rotation [$\alpha$]$_D^{28}$: −332.7° (c=1.165, chloroform)

EXAMPLE 3

(1S,4R)-5-[(S)-1-Phenylethoxy]-3-oxo-2-azabicyclo[2.2.0]hexa-5-ene

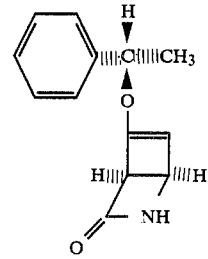

A solution of 100 mg of the compound obtained in Experiment 5 in 60 ml of acetonitrile was irradiated with light (longer than 300 nm) for 3 hours in an argon flow under cooling with ice water while stirring, using a high pressure mercury lamp of 100 W. The solvent was removed by distillation under reduced pressure and the resulting oily substance was subjected to medium pressure column chromatography [developing solvent: n-hexane-ethyl ether (1:1, v/v)] using 12 g of silica gel to obtain 40 mg of the product as an oily substance.

Infrared absorption spectrum (cm$^{-1}$, chloroform): 3420, 1755, 1618

$^1$H-NMR ($\delta$, CDCl$_3$): 1.58 (3H, d, J=7 Hz), 4.17 (2H, s), 4.80 (1H, s), 6.10 (1H, br), 7.30 (5H, s)

Mass spectrum (M+): 215

Rotation [$\alpha$]$_D^{30}$: +122.8° (c=1, chloroform)

Further in the column chromatography described above, crystals were obtained from eluting fractions subsequent to the compound described above. The crystals were recrystallized from ethyl ether-n-hexane to obtain 38 mg of the following compound as needles:

(1R,4S)-5-[(S)-1-Phenylethoxy]-3-oxo-2-azabicyclo[2.2.0]hexa-5-ene

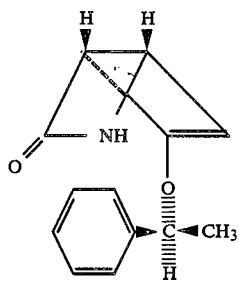

Melting point: 88°~89° C.

Infrared absorption spectrum (cm$^{-1}$, chloroform): 3420, 1752, 1618

$^1$H-NMR (δ, CDCl$_3$): 1.62 (3H, d, J=7 Hz), 4.19 (2H, s), 4.90 (1H, s), 5.06 (1H, q), 6.45 (1H, br), 7.30 (5H, s)

Mass spectrum (M+): 215

Rotation [α]$_D^{29}$: −279.4° (c=1, chloroform)

EXAMPLE 4

(1R,4R)-3,5-Dioxo-2-azabicyclo[2.2.0]hexane

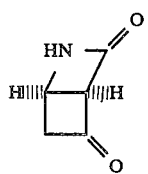

In a manner similar to Example 2, 54 mg of (1S,4R)-5-[(S)-1-phenylethoxy]-3-oxo-2-azabicyclo[2.2.0]hexa-5-ene was hydrolyzed and recrystallized to obtain 19 mg of the product as needles.

Melting point: 95°~96° C.

Rotation [α]$_D^{30}$: −340.8° (c=1.20, chloroform)

Infrared absorption spectrum and $^1$H-NMR (CDCl$_3$) spectrum were identical with those of the compound obtained in Example 2.

EXAMPLE 5

(1S,4R)-5-(1S,2S,5R-Menthoxy)-3-oxo-2-azabicyclo[2.2.0]hexa-5-ene

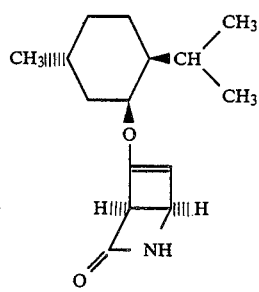

A solution of 400 mg of the compound obtained in Experiment 7 in 90 ml of ethyl ether was irradiated with light (longer than 300 nm) for 2 hours in an argon flow under cooling with ice water while stirring, using a high pressure mercury lamp of 400 W. The solvent was removed by distillation under reduced pressure and the residue was purified by silica gel column chromatography [developing solvent: n-hexane-ethyl acetate (4:1, v/v)] to obtain 400 mg of crystals. The crystals were washed with n-pentane. The n-pentane-soluble portion was concentrated to obtain 100 mg of the product as colorless crystals.

Melting point: 128°~129° C.

Infrared absorption spectrum (cm$^{-1}$, chloroform): 1750, 1610

$^1$H-NMR (δ, CDCl$_3$): 0.50~2.20 (18H, m), 4.08~4.36 (3H, m), 4.92 (1H, d, J=1 Hz), 6.03 (1H, br)

Rotation [α]$_D^{27}$: +233.75° (c=0.8, chloroform)

The n-pentane-insoluble portion in the preparation step described above was recrystallized from n-hexane to obtain 200 mg of the following compound as needles:

(1R,4S)-5-[(1S,2S,5R)-Menthoxy]-3-oxo-2-azabicyclo[2.2.0]hexa-5-ene

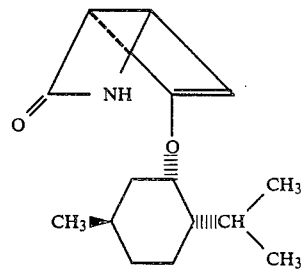

Melting point: 138°~139° C.

Infrared absorption spectrum (cm$^{-1}$, chloroform): 1750, 1610

$^1$H-NMR (δ, CDCl$_3$): 0.50~2.20 (18H, m), 4.08~4.36 (3H, m), 4.96 (1H, d, J=1 Hz), 5.58 (1H, br)

Rotation [α]$_D^{27.6}$: −85.42° (c=1.4, chloroform)

EXAMPLE 6

(1R,4R,5S)-5-Hydroxy-3-oxo-2-azabicyclo[2.2.0]hexane

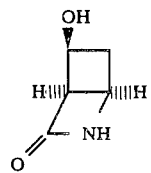

In 1.5 ml of tetrahydrofuran was dissolved 80 mg of the compound obtained in Example 2. Then 0.1 ml of acetic acid was added to the solution under ice cooling while stirring. Thereafter sodium cyanoborohydride was added to the mixture. The temperature was elevated to room temperature. After stirring for 3 hours, 2 ml of acetone was added and the mixture was stirred for 10 minutes. The mixture was allowed to stand overnight and then the reaction mixture was concentrated under reduced pressure. The residue was dissolved in a small quantity of methanol and the solution was purified by silica gel column chromatography [developing solvent: ethyl acetate-methanol (20:1)] to obtain 36 mg of the product as colorless crystals.

Melting point: 160°~162° C. (recrystallized from acetone)

Infrared absorption spectrum (cm$^{-1}$, KBr): 3200, 1715

$^1$H-NMR (δ, CD$_3$OD): 1.94 (1H, dd, J=14 Hz, 5 Hz), 2.68 (1H, ddd, J=14 Hz, 9 Hz, 5 Hz), 3.64~3.78 (1H, m), 3.82 (1H, dd, J=9 Hz, 3 Hz), 4.56 (1H, td, J=9 Hz, 5 Hz)

Rotation $[\alpha]_D^{27}$: +113.08° (c=1.13, methanol)

EXAMPLE 7

(1R,4R,5S)-5-Acetoxy-3-oxo-2-azabicyclo[2.2.0]hexane

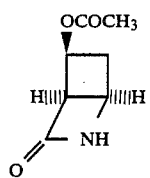

In 1 ml of acetic anhydride was suspended 17 mg of the compound obtained in Example 6, and 0.5 ml of pyridine was added to the suspension. After stirring for 1 hour, the reaction mixture was concentrated under reduced pressure. The crystalline residue was washed with n-hexane and recrystallized from ethyl ether-n-hexane to obtain 13 mg of the product as colorless needles.

Melting point: 86°~88° C.

Infrared absorption spectrum (cm$^{-1}$, KBr): 3250, 1745, 1715

$^1$H-NMR (δ, CDCl$_3$): 2.03 (3H, s), 2.16 (1H, ddd, J=13.5 Hz, 4.8 Hz, 1.0 Hz), 2.79 (1H, ddd, J=13.5 Hz, 8.8 Hz, 4.5 Hz), 3.78 (1H, ddd, J=4.5 Hz, 2.5 Hz, 1.0 Hz), 4.01 (1H, ddd, J=7.5 Hz, 2.5 Hz, 2.5 Hz), 5.13 (1H, ddd, J=8.8 Hz, 7.5 Hz, 4.8 Hz), 6.5~6.9 (1H, br)

Rotation $[\alpha]_D^{25}$: −19.57° (c=0.77, chloroform)

EXPERIMENT 8

(S)-4-[(Methoxycarbonyl)methyl]azetidin-2-one:

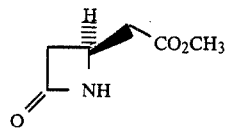

The compound, 23.5 mg, obtained in Example 2 was heated together with 2 ml of absolute methanol under reflux. The reaction mixture was concentrated under reduced pressure and the residue was purified by silica gel column chromatography [2 g, developing solvent: ethyl ether] to obtain 27.3 mg of the product as crystals.

Melting point: 69°~70° C.; 70.5°~71.5° C. when recrystallized from ethyl ether

Infrared absorption spectrum (cm$^{-1}$, chloroform): 3420, 1755, 1730

$^1$H-NMR (δ, CDCl$_3$): 2.4~3.4 (4H, m), 3.72 (3H, s), 3.92 (1H, m), 6.33 (1H, bs)

Rotation $[\alpha]_D^{29}$: +65.5° (c=1.20, chloroform)

While the invention has been described in detail and with reference to specific embodiments thereof, it will be apparent to one skilled in the art that various changes and modifications can be made therein without departing from the spirit thereof.

What is claimed is:

1. A 3-oxo-2-azabicyclohexane derivative represented by the formula:

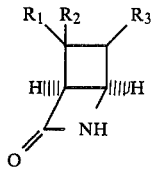

wherein R$_1$ represents an optically active menthoxy group or an optically active 1-phenylethoxy group, and R$_2$ and R$_3$ are combined to form a bond; or R$_3$ is a hydrogen atom, and R$_1$ and R$_2$ are combined to form an oxo group.

2. A compound as claimed in claim 1 which is (1R,4R)-3,5-dioxo-2-azabicyclo[2.2.0]hexane.

3. A compound as claimed in claim 1 which is (1S,4R)-5-[(1S,2S,5R)-menthoxy]-3-oxo-2-azabicyclo[2.2.0]hexa-5-ene.

4. A compound as claimed in claim 1 which is (1S,4R)-5-[(S)-1-phenylethoxy]-3-oxo-2-azabicyclo[2.2.0]hexa-5-ene.

5. A compound as claimed in claim 1 which is (1S,4R)-5-[(l)-menthoxy]-3-oxo-2-azabicyclo[2.2.0]hexa-5-ene.

* * * * *